US008173801B2

(12) United States Patent
Viscomi et al.

(10) Patent No.: US 8,173,801 B2
(45) Date of Patent: *May 8, 2012

(54) PROCESSES FOR THE PRODUCTION OF POLYMORPHIC FORMS OF RIFAXIMIN

(75) Inventors: Giuseppe Claudio Viscomi, Bologna (IT); Manuela Campana, Bologna (IT); Dario Braga, Bologna (IT); Donatella Confortini, Bologna (IT); Vincenzo Cannata, Bologna (IT); Paolo Righi, Bologna (IT); Goffredo Rosini, Bologna (IT)

(73) Assignee: Alfa Wassermann, S.p.A., Bologna (IT)

(*) Notice: Subject to any disclaimer, the term of this patent is extended or adjusted under 35 U.S.C. 154(b) by 0 days.

This patent is subject to a terminal disclaimer.

(21) Appl. No.: 13/041,346

(22) Filed: Mar. 4, 2011

(65) Prior Publication Data

US 2011/0160449 A1    Jun. 30, 2011

Related U.S. Application Data

(63) Continuation of application No. 12/119,612, filed on May 13, 2008, now Pat. No. 7,923,553, which is a continuation-in-part of application No. 11/873,841, filed on Oct. 17, 2007, now Pat. No. 7,915,275, which is a continuation-in-part of application No. 11/135,651, filed on May 24, 2005, now abandoned, which is a continuation-in-part of application No. PCT/EP2004/012490, filed on Nov. 4, 2004.

(30) Foreign Application Priority Data

Nov. 7, 2003  (IT) .............................. MI2003A2144

(51) Int. Cl.
*C07D 498/22* (2006.01)
(52) U.S. Cl. ..................................................... 540/456
(58) Field of Classification Search .................. 540/456
See application file for complete search history.

(56) References Cited

U.S. PATENT DOCUMENTS

| 4,341,785 | A | 7/1982 | Marchi et al. |
| 4,557,866 | A | 12/1985 | Cannata et al. |
| 7,045,620 | B2 | 5/2006 | Viscomi et al. |
| 2009/0028940 | A1 | 1/2009 | Jahagirdar et al. |
| 2009/0082558 | A1 | 3/2009 | Kothakonda et al. |
| 2009/0312357 | A1 | 12/2009 | Rao et al. |

FOREIGN PATENT DOCUMENTS

| CA | 1215976 | 12/1986 |
| CA | 1218650 | 3/1987 |
| EP | 0161534 A2 | 11/1985 |
| EP | 1698630 A1 | 9/2006 |
| EP | 1557421 B1 | 5/2007 |
| EP | 2011486 A1 | 1/2009 |
| IT | MI2005A000345 | 3/2005 |
| WO | 2008/155728 A1 | 12/2008 |
| WO | 2009/008005 A1 | 1/2009 |
| WO | 2009/047801 A1 | 4/2009 |
| WO | 2009/108730 A2 | 9/2009 |

OTHER PUBLICATIONS

European Patent No. 1 557 421, Reply to the Communication pursuant to Article 96(2), May 2, 2006.
European Patent No. 1 557 421, Opposition Proceedings, "Notice of opposition to a European patent," Feb. 11, 2008.
European Patent No. 1 557 421, Opposition Proceedings, Patentee response to Notice of Opposition, Sep. 10, 2008.
European Patent No. 1 557 421, Opposition Proceedings, Opinion of the Opposition Division, Jan. 19, 2009.
European Patent No. 1 557 421, Opposition Proceedings, Patentee response to summons to attend oral proceedings, Apr. 22, 2009.
European Patent No. 1 557 421, Opposition Proceedings, Opponent response to summons to attend oral proceedings, Apr. 29, 2009.
European Patent No. 1 557 421, Opposition Proceedings, Patentee response to brief communication, May 29, 2009.
European Patent No. 1 557 421, Opposition Proceedings, European Patent Office Decision rejecting the opposition, Jul. 8, 2009.
European Patent No. 1 557 421, Opposition Proceedings, Appellant Notice of Appeal, Sep. 18, 2009.
European Patent No. 1 557 421, Opposition Proceedings, Appellant Statement of Grounds for Appeal, Nov. 18, 2009.
Alvisi, V. et al., "Treatment of Secretory Diarrhoeas—A Double-Blind Trial of the Effectiveness of Rifaximin (L 105) and Neomycin," Clinical Trials Journal, 1984, 21, No. 4, pp. 215-223.
Rodriguez-Spong, B. et al., "General Principles of Pharmaceutical Solid Polymorphism: a Supramolecular Perspective," Advanced Drug Delivery Reviews, 56 (2004), 241-274.
Morris, K.R. et al., "Theoretical Approaches to Physical Transformations of Active Pharmaceutical Ingredients During Manufacturing Processes," Advanced Drug Delivery Reviews, 48 (2001), 91-114.

(Continued)

Primary Examiner — Bruck Kifle
(74) Attorney, Agent, or Firm — Sam K. Tahmassebi; TechLaw LLP

(57) ABSTRACT

Crystalline polymorphous forms of rifaximin (INN) antibiotic named rifaximin α and rifaximin β, and a poorly crystalline form named rifaximin γ, useful in the production of medicinal preparations containing rifaximin for oral and topical use and obtained by means of a crystallization carried out by hot-dissolving the raw rifaximin in ethyl alcohol and by causing the crystallization of the product by addition of water at a determinate temperature and for a determinate period of time, followed by a drying carried out under controlled conditions until reaching a settled water content in the end product, are the object of the invention.

19 Claims, 3 Drawing Sheets

OTHER PUBLICATIONS

Viscomi, G.C. et al., "Crystal Forms of Rifaximin and Their Effect on Pharmaceutical Properties," CrysEngComm, 2008, 10, 1074-1081.

Brufani, M. et al., "X-Ray Crystal Structure of 4-Deoxy-3'-bromopyrido[1',2'-1,2]imidazo[5,4-c]rifamycin S," The Journal of Antibiotics, 37:12, 1623-1627 (Dec. 1984).

Soro, O. et al., "Selection of Rifampicin-Resistant Mycobacterium Tuberculosis Does Not Occur in the Presence of Low Concentrations of Rifaximin," Clin Microbiol Infect, 1997, 3:147-151.

TicinumLab. Example 7, Patent EP 0 161 534, "Synthesis of 4-Deoxy-4'methyl-pyrido-[1',2':1,2]imidazo]5,4-c]ryfamicin SV.", (2009).

TicinumLab. Example 9, Patent EP 0 161 534, "Synthesis of 4-Deoxy-4'methyl-pyrido-[1',2':1,2]imidazo]5,4-c]ryfamicin SV.", (2009).

Department of Health and Human Services, Certificate of GMP Compliance of a Manufacturer, Nov. 16, 2007.

European Medicines Industry, ICH Topic Q6A, Specifications: Test Procedures and Acceptance Criteria for New Drug Substances and New Drug Products: Chemical Substances, pp. 1-32, 2000.

Henwood, S.Q. et al., "Solubility and Dissolution Properties of Generic Rifampicin Raw Materials," Drug Development and Industrial Pharmacy, 26(4), 403-408 (2000).

Morris, K.R. "Polymorphism in Pharmaceutical Solids," in "Structural Aspects of Hydrates and Sovates," H.G. Brittain editor, Drugs and the Pharmaceutical Sciences, vol. 95, Chapter 4, pp. 125-181, 1999.

Rifaximin—Intrinsic Dissolution Experimental Data, Apr. 2009.

Bacchi, A. et al., "Sampling Rifamycin Conformational Variety by Cruising Through Crystal Forms: Implications for Polymorph Screening and for Biological Models," New J. Chem., 2008, 32, 1725-1735.

Venturini, A.P. "Pharmacokinetics of L/105, a New Rifamycin, in Rats and Dogs, after Oral Administration,"Chemotherapy 29:1-3 (1983).

Pelizza, G. "Polymorphism of Rifampicin," II Farmaco—Ed. Sc., vol. 32, No. 7, pp. 471-481, 1977.

Rao, R.N. et al., "O-Line 2D-LC-ESI/MS/MS Determination of Rifaximin in Rat Serum," Biomed. Chromatogr. 2009, 1-6.

Descombe, J.J. et al., "Pharmacokinetic Study of Rifaximin After Oral Administration in Healthy Volunteers," Int. J. Clin. Pharm. Res. XIV(2), 51-56 (1994).

Rossi, C. et al., "NMR Investigation of a New Semisynthetic Bioactive Compound," Bulletin of Magnetic Resonance, 1996, vol. 18, No. 1-2, pp. 87-90.

Italian Product Label for NORMIX (rifaximin), Apr. 23, 1985.

Cellai, L. et al., "A Study of Structure-Activity Relationships in 4-Deoxypyrido[1',2'-1,2] imidazo[5,4-c]rifamycin SV Derivatives by Electron Spectroscopy for Chemical Analysis and 1H NMR," Molecular Pharmacology, 27:103-108, 1984.

European Patent No. 1 557 421, Opposition Proceedings, "Opponent Response to the Late Submissions of Patentee," Jun. 11, 2009.

European Patent No. 1 557 421, Opposition Proceedings, "Patentee Response to Opponent Statement Setting Out the Grounds of Appeal," Jun. 2, 2010.

Zach Systems SPA, "Synthesis of rifaximin obtained according to examples 7 and 9 reported in European Patent EP0161534," May 13, 2010.

PROCESSES FOR THE PRODUCTION OF POLYMORPHIC FORMS OF RIFAXIMIN

APPLICATION PRIORITY DATA

This application is a continuation of U.S. application Ser. No. 12/119,612, filed May 13, 2008, which in turn is a continuation-in-part of application U.S. application Ser. No. 11/873,841, filed on Oct. 17, 2007, which is a continuation-in part of U.S. application Ser. No. 11/135,651, filed on May 24, 2005, now abandoned, which is a continuation-in-part of PCT/EP04/12490, filed on Nov. 4, 2004 which claims priority to Italian application No. MI2003A002144 filed Nov. 7, 2003, all of which are incorporated by reference herein in their entirety, including any drawings.

BACKGROUND AND SUMMARY OF THE INVENTION

Rifaximin (INN; see The Merck Index, XIII Ed., 8304) is an antibiotic belonging to the rifamycin class, exactly it is a pyrido-imidazo rifamycin described and claimed in Italian Patent IT 1154655, while European Patent EP 0161534 describes and claims a process for its production starting from rifamycin O (The Merck Index, XIII Ed., 8301).

Both these patents describe the purification of rifaximin in a generic way stating that crystallization can be carried out in suitable solvents or solvent systems and summarily showing in some examples that the reaction product can be crystallized from the 7:3 mixture of ethyl alcohol/water and can be dried both under atmospheric pressure and under vacuum without specifying in any way either the experimental conditions of crystallization and drying, or any distinctive crystallographic characteristic of the obtained product.

The presence of different polymorphs had just not been noticed and therefore the experimental conditions described in both patents had been developed with the goal to get a homogeneous product having a suitable purity from the chemical point of view, independent from the crystallographic aspects of the product itself.

It has now been found, unexpectedly, that there are several polymorphous forms whose formation, besides the solvent, depends on time and temperature conditions under which both crystallization and drying are carried out.

In the present application, these orderly polymorphous forms will be, later on, conventionally identified as rifaximin α (FIG. 1) and rifaximin β (FIG. 2) on the basis of their respective specific diffractograms, while the poorly crystalline form with a high content of amorphous component will be identified as rifaximin γ (FIG. 3).

Rifaximin polymorphous forms have been characterized through the technique of the powder X-ray diffraction.

The identification and characterization of these polymorphous forms and, simultaneously, the definition of the experimental conditions for obtaining them is very important for a compound endowed with pharmacological activity which, like rifaximin, is marketed as medicinal preparation, both for human and veterinary use. In fact it is known that the polymorphism of a compound that can be used as active ingredient contained in a medicinal preparation can influence the pharmaco-toxicologic properties of the drug. Different polymorphous forms of an active ingredient administered as drug under oral or topical form can modify many properties thereof like bioavailability, solubility, stability, colour, compressibility, flowability and workability with consequent modification of the profiles of toxicological safety, clinical effectiveness and productive efficiency.

What mentioned above is confirmed by the fact that the authorities that regulate the grant of marketing authorization of the drugs market require that the manufacturing methods of the active ingredients are standardized and controlled in such a way that they give homogeneous and sound results in terms of polymorphism of production batches (CPMP/QWP/96, 2003—Note for Guidance on Chemistry of new Active Substance; CPMP/ICH/367/96—Note for guidance specifications: test procedures and acceptance criteria for new drug substances and new drug products: chemical substances; Date for coming into operation: May 2000).

The need for the above-mentioned standardization has further been strengthened in the field of the rifamycin antibiotics by Henwood S. Q., de Villiers M. M., Liebenberg W. and Lötter A. P., Drug Development and Industrial Pharmacy, 26 (4), 403-408, (2000), who have ascertained that different production batches of the rifampicin (INN) made from different manufacturers differ from each other in that they show different polymorphous characteristics, and as a consequence they show different dissolution profiles, along with a consequent alteration of the respective pharmacological properties.

By applying the crystallization and drying processes generically disclosed in the previous patents IT 1154655 and EP 0161534 it has been found that under some experimental conditions a poorly crystalline form of rifaximin is obtained, while under other experimental conditions other polymorphic crystalline forms of rifaximin is obtained. Moreover it has been found that some parameters, absolutely not disclosed in the above-mentioned patents, like for instance preservation conditions and the relative ambient humidity, have the surprising effect to determine the polymorph form.

The polymorphous forms of rifaximin object of the present patent application were never seen or hypothesized, while thinking that, whichever method was used within the range of the described condition, a sole homogeneous product would always have been obtained, irrespective of crystallizing, drying and preserving conditions.

It has now been found that the formation of α, β and γ forms both depends on the presence of water within the crystallization solvent, on the temperature at which the product is crystallized and on the amount of water present in the product at the end of the drying phase.

Form α, form β and form γ of rifaximin have then been synthesized and they are the object of the invention.

Moreover it has been found that the presence of water in rifaximin in the solid state is reversible, so that water absorption and/or release can take place in time in presence of suitable ambient conditions; consequently rifaximin is susceptible of transition from one form to another, also remaining in the solid state, without need to be again dissolved and crystallized. For instance polymorph α, getting water by hydration up to a content higher than 4.5%, turns into polymorph β, which in its turn, losing water by drying up to a content lower than 4.5%, turns into polymorph α.

These results have a remarkable importance as they determine the conditions of industrial manufacturing of some steps of working which could not be considered critical for the determination of the polymorphism of a product, like for instance the washing of a crystallized product, or the preservation conditions of the end product, or the characteristics of the container in which the product is preserved.

The above-mentioned α, β and γ forms can be advantageously used as pure and homogeneous products in the manufacture of medicinal preparations containing rifaximin.

As already said, the process for manufacturing rifaximin from rifamycin O disclosed and claimed in EP 0161534 is deficient from the point of view of the purification and identification of the product obtained; it shows some limits also from the synthetic point of view as regards, for instance, the very long reaction times, from 16 to 72 hours, not very suitable to an industrial use and moreover because it does not provide for the in situ reduction of rifaximin oxidized that may be formed within the reaction mixture.

Therefore, a further object of the present invention is an improved process for the industrial manufacturing of the α, β and γ forms of rifaximin, herein claimed as products and usable as defined and homogeneous active ingredients in the manufacture of the medicinal preparations containing such active ingredient.

DESCRIPTION OF THE INVENTION

Figure 1:
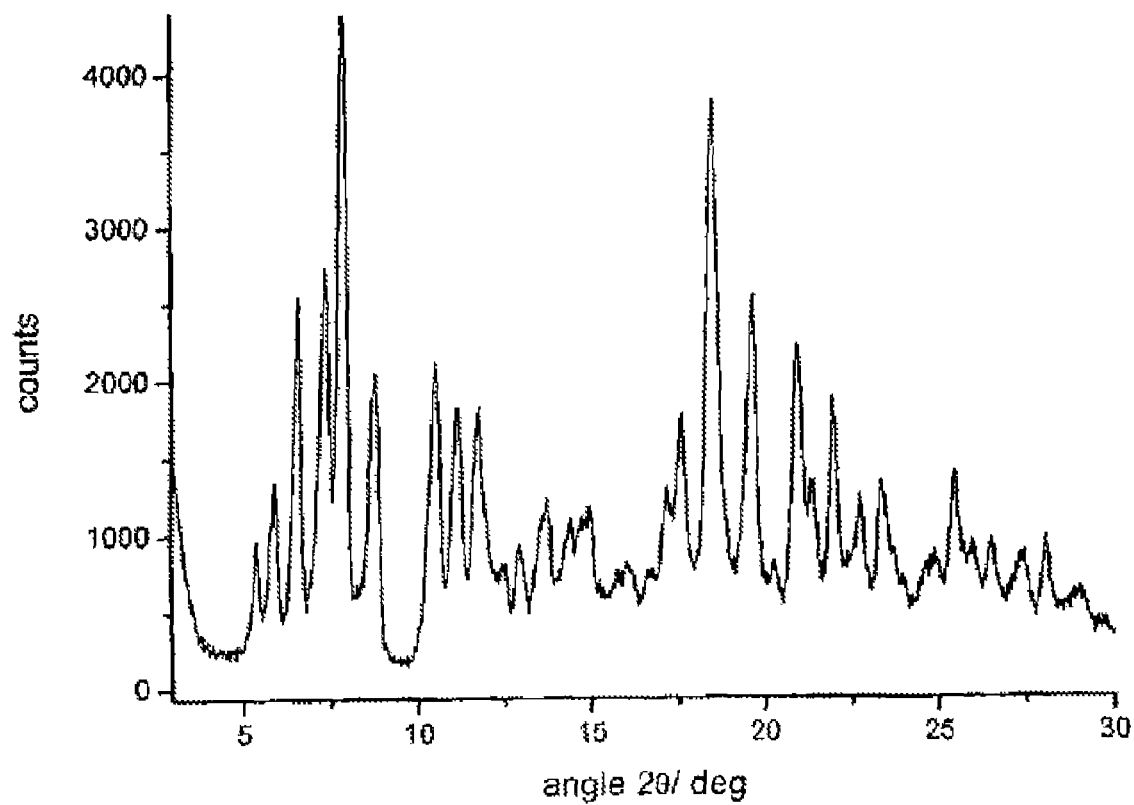
FIG. 1 is a powder X-ray diffractogram of rifaximin polymorphic form α.

As already said, form α, form β and form γ of the antibiotic known as rifaximin (INN), processes for their production and the use thereof in the manufacture of medicinal preparations for oral or topical route, are object of the present invention.

A process object of the present invention comprises reacting one molar equivalent of rifamycin O with an excess of 2-amino-4-methylpyridine, preferably from 2.0 to 3.5 molar equivalents, in a solvent mixture consisting of water and ethyl alcohol in volumetric ratios between 1:1 and 2:1, for a period of time between 2 and 8 hours at a temperature between 40° C. and 60° C.

When the reaction is over, the reaction mass is cooled at room temperature and is added with a solution of ascorbic acid in a mixture of water, ethyl alcohol and aqueous concentrated hydrochloric acid, under strong stirring, in order to reduce the small amount of oxidized rifaximin that forms during the reaction and finally the pH is adjusted to about 2.0 by a further addition of hydrochloric acid concentrated aqueous solution, in order to better remove the excess of 2-amino-4-methylpyridine used in the reaction. The suspension is filtered and the obtained solid is washed with the same water/ethyl alcohol solvent mixture used in the reaction. Such semi finished product is called "raw rifaximin".

Raw rifaximin can be directly submitted to the subsequent purification step. Alternatively, in case long times of preservation of the semi finished product are expected, raw rifaximin can be dried under vacuum at a temperature lower than 65° C. for a period of time between 6 and 24 hours; such semi finished product is called "dried raw rifaximin".

The so obtained raw rifaximin and/or dried raw rifaximin are purified by dissolution in ethyl alcohol at a temperature between 45° C. and 65° C. and by crystallization by addition of water, preferably in weight amounts between 15% and 70% in respect of the amount by weight of the ethyl alcohol used for the dissolution, and keeping the obtained suspension at a temperature between 50° C. and 0° C. under stirring during a period of time between 4 and 36 hours.

The suspension is filtered and the obtained solid is washed with water and dried under vacuum or under normal pressure, with or without a drying agent, at a temperature between room temperature and 105° C. for a period of time between 2 and 72 hours.

The achievement of α, β and γ forms depends on the conditions chosen for crystallization. In particular, the composition of the solvent mixture from which crystallization is carried out, the temperature at which the reaction mixture is kept after crystallization and the period of time at which that temperature is kept, have proven to be critical.

More precisely, rifaximin γ is obtained when the solution is taken to a temperature between 28° C. and 32° C. in order to start precipitation and the obtained suspension is further cooled to 0° C. and kept at this temperature for a period of time between 6 and 24 hours.

The suspension is filtered, the solid is washed with demineralized water and dried to a water content between 1.0% and 2.0%.

α and β rifaximins are obtained when the temperature is first taken to a value between 28° C. and 32° C. to start crystallization, then the suspension is taken to a temperature between 40° C. and 50° C. and kept at this value for a period of time between 6 and 24 hours, then the suspension is quickly cooled to 0° C., in a period of time between 15 minutes and one hour, is filtered, the solid is washed with water and then is dried.

The drying step plays an important role in obtaining the α and β polymorphous forms of rifaximin and must be checked with a suitable method fit for the water dosage, like for instance the Karl Fischer method, in order to check the amount of remaining water present in the product under drying.

The obtaining of rifaximin α or of rifaximin β during drying in fact depends on the final water residual content, higher or lower than 4.5%, and not from the experimental conditions of pressure and temperature at which this critical limit of water percent is achieved. The two polymorphous forms, with higher or lower water content, can be obtained by drying under vacuum or at atmospheric pressure, at room temperature or at high temperatures, with or without drying agents, provided that drying is prolonged for the time necessary so that the water percent characteristic for each polymorphous form is achieved.

Polymorphous form β is obtained when the drying of the product crystallized and washed with water is stopped at values of water higher than 4.5%, measured with the Karl Fisher method, preferably between 5.0% and 6.0%, whereas if drying continues to values lower than 4.5%, preferably between 2.0% and 3.0%, polymorphous form α is obtained.

Both form γ and forms α and β of rifaximin are hygroscopic, absorb water in a reversible way in time in the presence of suitable conditions of pressure and humidity in the ambient and are susceptible of transformation from one form to another.

Polymorphous form α, kept in an ambient with a relative humidity higher than 50% for a period of time between 12 and 48 hours, turns into the polymorphous form β, which in its turn, by drying until getting an amount of water lower than 4.5%, preferably comprised between 2.0% and 3.0%, turns into the polymorphous form α.

Another type of transition takes place between form γ and forms α and β, depending upon the temperatures kept during the phase of precipitation of rifaximin.

In particular form γ turns into forms α or β by keeping a suspension of form γ of rifaximin in a solvent mixture ethyl alcohol/water 7:3 (V/V) at a temperature between 38° C. and 50° C. under strong stifling for a prolonged period of time, preferably comprised between 6 and 36 hours.

After filtration and washing with demineralized water, drying up to a water content higher than 4.5%, preferably between 5.0% and 6.0%, gives the polymorphous form β, whereas if drying continues up to a water content lower than 4.5%, preferably between 2.0% and 3.0%, form α is obtained.

Rifaximins α and β turn can turn into rifaximin γ by dissolution in ethyl alcohol and by treatment of the resulting solution as previously described for the preparation of form γ.

These transitions from one form to another result to be very important in the scope of the invention, because they can be an alternative manufacturing method to obtain the form desired for the production of the medicinal preparations. Therefore both the process that allows to turn rifaximin γ into rifaximin α or β in a valid way from an industrial standpoint, the process that allows to turn rifaximin α into Rifaximin β in a valid way from an industrial stand point or vice versa rifaximin β into rifaximin α, are important part of the invention.

The process concerning the transformation of rifaximin γ into rifaximin α or rifaximin β comprises suspending rifaximin γ in a solvent mixture consisting of ethyl alcohol/water in a 7:3 volumetric ratio, heating the suspension up to a temperature between 38° C. and 50° C. and keeping it at this temperature under strong stifling for a period of time between 6 and 36 hours. The suspension is then filtered, the solid is washed with water and dried getting the polymorphous form β when drying is carried on until a water percent between 5.0% and 6.0% measured with the Karl Fischer method, and polymorphous form α when drying is continued until a water percent between 2.0% and 3.0% is reached.

The process for getting form γ starting from rifaximin α or β comprises dissolving under stirring, at a temperature between 50° C. and 60° C., α or β form in ethyl alcohol, adding demineralized water until reaching a 7:3 ethyl alcohol/water volumetric ratio, cooling the solution under strong stifling to 30° C., cooling the abundant precipitate to 0° C. and keeping the suspension under stirring at 0° C. for a period of time between 6 and 24 hours. The suspension is then filtered, the solid is washed with water and dried up to a water percent lower than 2.0% thus obtaining rifaximin γ.

The process concerning the transformation of form α into form β consists in keeping rifaximin α, in the powder form, in an ambient having a rate of relative humidity higher than 50% for the required amount of time, generally between 12 and 48 hours, in order to get a water content in the powder higher than 4.5%.

The process concerning the transformation of form β into form α consists in submitting the powder of rifaximin β to a drying process under vacuum or under conditions of normal pressure, with or without a drying agent, at a temperature between the room temperature and 105° C., for a period of time between 2 and 72 hours, in order to get a water content in the powder lower than 4.5%, preferably between 2.0% and 3.0%.

From what said above, it results that during the phase of preservation of the product particular care has to be taken so that ambient conditions do not change the water content of the product, by preserving the product in an ambient having controlled humidity or in closed containers that do not allow a significant exchange of water with the exterior ambient.

Figure 2:
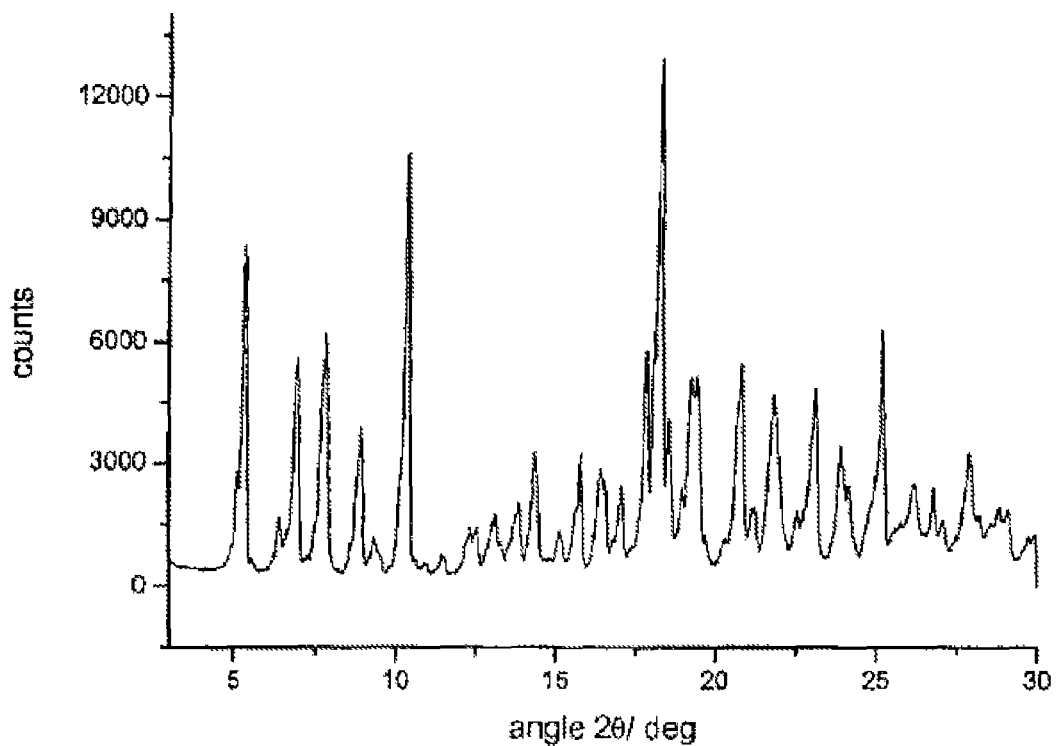
FIG. 2 is a powder X-ray diffractogram of rifaximin polymorphic form β.

The polymorph called rifaximin α is characterized by a water content lower than 4.5%, preferably between 2.0% and 3.0% and from a powder X-ray diffractogram (reported in FIG. 1) which shows peaks at the values of the diffraction angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°. The polymorph called rifaximin β is characterized by a water content higher than 4.5%, preferably between 5.0% and 6.0%, and by a powder X-ray diffractogram (reported in FIG. 2) which shows peaks at the values of the diffraction angles 2θ of 5.4°; 6.4°; 7.0°; 7.8°; 9.0°; 10.4°; 13.1°; 14.4°; 17.1°; 17.9°; 18.3°; 20.9°.

Figure 3:
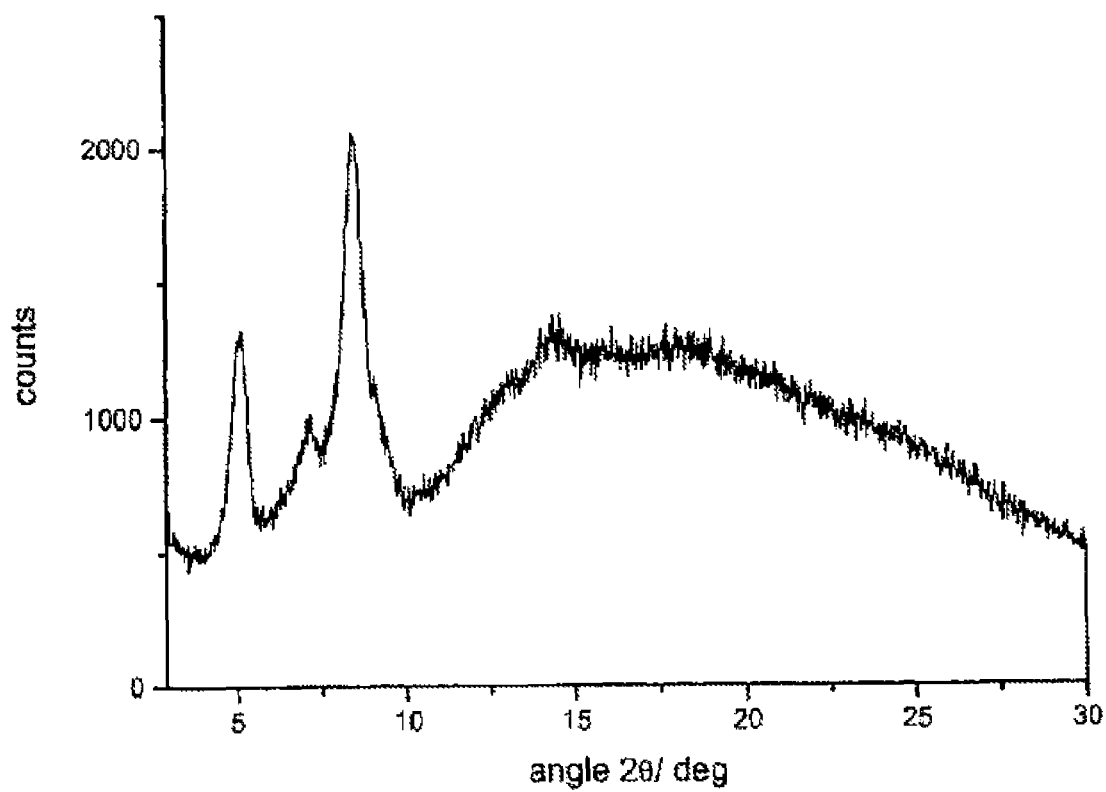
FIG. 3 is a powder X-ray diffractogram of rifaximin polymorphic form γ.

The polymorph called rifaximin γ is characterized by a powder X-ray diffractogram much poorer because of the poor crystallinity; the significant peaks are at the values of the diffraction angles 2θ of 5.0°; 7.1°; 8.4° as reported in FIG. 3.

The diffractograms have been carried out by means of the Philips X'Pert instrument endowed with Bragg-Brentano geometry and under the following working conditions:
X-ray tube: Copper
Radiation used: K (α1), K (α2)
Tension and current of the generator: KV 40, mA 40
Monocromator: Graphite
Step size: 0.02
Time per step: 1.25 seconds
Starting and final angular 2θ value: 3.0°÷30.0°

The evaluation of the water content present in the analyzed samples has always been carried out by means of the Karl Fischer method.

Forms α, β and γ can be advantageously used in the production of medicinal preparations having antibiotic activity, containing rifaximin, for both oral and topical use. The medicinal preparations for oral use contain rifaximin α or β or γ together with the usual excipients as diluting agents like mannitol, lactose and sorbitol; binding agents like starches, gelatines, sugars, cellulose derivatives, natural gums and polyvinylpyrrolidone; lubricating agents like talc, stearates, hydrogenated vegetable oils, polyethylenglycol and colloidal silicon dioxide; disintegrating agents like starches, celluloses, alginates, gums and reticulated polymers; coloring, flavoring and sweetening agents.

All the solid preparations administrable by oral route can be used in the scope of the present invention, for instance coated and uncoated tablets, capsules made of soft and hard gelatine, sugar-coated pills, lozenges, wafer sheets, pellets and powders in sealed packets.

The medicinal preparations for topical use contain rifaximin α or β or γ together with the usual excipients like white petrolatum, white wax, lanoline and derivatives thereof, stearylic alcohol, propylenglycol, sodium lauryl sulfate, ethers of the fatty polyoxyethylene alcohols, esters of the fatty polyoxyethylene acids, sorbitan monostearate, glyceryl monostearate, propylene glycol monostearate, polyethylene glycols, methylcellulose, hydroxypropylmethylcellulose, sodium carboxymethylcellulose, colloidal aluminium and magnesium silicate, sodium alginate.

All topical preparations can be used in the scope of the present invention, for instance ointments, pomades, creams, gels and lotions.

The invention is herein below illustrated by some non-limiting examples: from what described it is evident that forms α, β and γ can be obtained by suitably combining between them the above mentioned conditions of crystallization and drying.

EXAMPLE 1

Preparation of Raw Rifaximin α and of Dried Raw Rifaximin

In a three-necked flask equipped with mechanic stirrer, thermometer and reflux condenser, 120 ml of demineralized water, 96 ml of ethyl alcohol, 63.5 g of rifamycin O and 27.2 g of 2-amino-4-methylpyridine are loaded in succession at room temperature. After loading, the mass is heated at 47±3° C., is kept under stifling at this temperature for 5 hours, then is cooled to 20±3° C. and, in 30 minutes, is added with a mixture, prepared separately, consisting of 9 ml of demineralized water, 12.6 ml of ethyl alcohol, 1.68 g of ascorbic acid and 9.28 g of aqueous concentrated hydrochloric acid. When the addition is over, the mass is kept under stirring for 30 minutes at an inner temperature of 20±3° C. and then, at the same temperature, 7.72 g of concentrated hydrochloric acid are dropped until pH 2.0.

When the addition is over, the mass is kept under stirring, still at an inner temperature of 20° C., for 30 minutes, then the precipitate is filtered and washed with a mixture consisting of 32 ml of demineralized water and 25 ml of ethyl alcohol. The obtained "raw rifaximin" (89.2 g) is dried under vacuum at room temperature for 12 hours yielding 64.4 g of "dried raw rifaximin" having a 5.6% water content and a diffractogram corresponding to polymorphous form β. The product is further dried under vacuum until constant weight yielding 62.2 g of dried raw rifaximin having a 2.2% water content, whose diffractogram corresponds to polymorphous form α.

The product is hygroscopic and the obtained polymorphous form is reversible: polymorphous form α absorbs water from the atmospheric humidity until reaching, depending upon the relative humidity and the time of exposure, a water content higher than 4.5% and turning into polymorphous form β which in its turn, by drying loses part of the water turning into polymorphous form α with a water content between 2.0% and 3.0%.

EXAMPLE 2

Preparation of Rifaximin γ

163 ml of ethyl alcohol and 62.2 g of dried raw rifaximin are loaded at room temperature into a three-necked flask equipped with mechanic stirrer, thermometer and reflux condenser. The suspension is heated at 57±3° C. under stifling until complete dissolution of the solid and at this temperature 70 ml of demineralized water are added in 30 minutes. When the addition is over the temperature is brought to 30° C. in 40 minutes and is kept at this value until abundant crystallization, then the temperature is further lowered to 0° C. during 2 hours and kept at this value for 6 hours. The suspension is then filtered and the solid is washed with 180 g of demineralized water.

After drying under vacuum at room temperature until constant weight, 52.7 g of pure rifaximin γ are obtained with a 1.5% water content.

Form γ is characterized by a powder X-ray diffractogram showing significant peaks at diffraction angles 2θ of 5.0°; 7.1°; 8.4°.

EXAMPLE 3

Preparation of Rifaximin α

62.2 g of dried raw rifaximin and 163 ml of ethyl alcohol are loaded at room temperature into a three-necked flask equipped with mechanic stirrer, thermometer and reflux condenser. The suspension is heated at 57±3° C. until complete dissolution of the solid and then 70 ml of demineralized water are added at this temperature during 30 minutes. When addition is over the temperature is taken to 30° C. for 40 minutes and is kept at this value until abundant crystallization. The suspension temperature is then taken to about 40° C. and kept at this value during 20 hours under stirring; then the temperature is taken to 0° C. in 30 minutes and the suspension is immediately filtered. The solid is washed with 180 ml of demineralized water and dried under vacuum at room temperature until constant weight; 51.9 g of rifaximin form α are obtained with a 2.5% water content and a powder X-ray diffractogram showing peaks at values of angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°.

EXAMPLE 4

Preparation of Rifaximin α

89.2 g of raw rifaximin and 170 ml of ethyl alcohol are loaded at room temperature into a three-necked flask equipped with mechanic stirrer, thermometer and reflux condenser, then the suspension is heated at 57±3° C. until complete dissolution of the solid. The temperature is taken to 50° C. and then 51.7 ml of demineralized water are added at this temperature in 30 minutes. When addition is over the temperature is taken to 30° C. in one hour and the suspension is kept for 30 minutes at this temperature obtaining a abundant crystallization. The suspension temperature is taken to 40° C. and kept at this value for 20 hours under stifling and then further lowered to 0° C. in 30 minutes, after which the suspension is immediately filtered. The solid is washed with 240 ml of demineralized water and dried under vacuum at 65° C. until constant weight obtaining 46.7 g of rifaximin α with a 2.5% water content.

EXAMPLE 5

Preparation of Rifaximin α

Example 3 is repeated by increasing to 50° C. the temperature at which the suspension is kept and lowering to 7 hours the time in which the suspension is kept at this temperature. The obtained product is equal to that of example 3.

EXAMPLE 6

Preparation of Rifaximin β

Crystallization of dried raw rifaximin is carried out according to the method described in example 3. The drying under vacuum at room temperature is checked by means of the Karl Fischer method and is stopped when the water content reaches 5.0%: 52.6 g of rifaximin β are obtained characterized by a powder X-ray diffractogram showing peaks at values of angles 2θ of 5.4°; 6.4°; 7.0°; 7.8°; 9.0°; 10.4°; 13.1°, 14.4°; 17.1°; 17.9°; 18.3°; 20.9°.

EXAMPLE 7

Preparation of Rifaximin α Starting from Rifaximin γ

5 Grams of rifaximin γ are suspended in a mixture consisting of 13 ml of ethyl alcohol and 5.6 ml of water and the suspension is heated at 40° C. for 24 hours under stifling in a 50 ml flask equipped with condenser, thermometer and mechanic stirrer. The suspension is then filtered and the solid is washed with water and then dried under vacuum at room temperature until constant weight. 4 g of rifaximin are obtained showing a powder X-ray diffractogram corresponding to that of the polymorphous form α and a 2.6% water content.

EXAMPLE 8

Preparation of Rifaximin γ Starting from Rifaximin α

15 Grams of rifaximin form α and 52.4 ml of ethyl alcohol are loaded into a 250 ml three-necked flask equipped with reflux condenser, thermometer and mechanical stirrer; the suspension is heated under stirring at the temperature of 50° C. until complete dissolution of the solid.

The limpid solution is added with 22.5 ml of water for 30 minutes under stirring, cooled to 30° C. and kept at this temperature for 30 minutes. The formed suspension is cooled to 0° C. under strong stifling and kept at this temperature during 6 hours. A part of the suspension is taken after this period of time, filtered, washed with demineralized water and dried under vacuum at 30° C. until constant weight.

The obtained product, 3.7 g, shows a diffractogram consistent with that of form γ and α 1.7% water content.

The remaining part of the suspension is kept at 0° C. for further 18 hours under strong stirring and then is filtered, washed with demineralized water and dried at 30° C. under vacuum until constant weight. 9 g of product showing a diffractogram consistent with that of form γ and a 1.6% water content are obtained.

EXAMPLE 9

Preparation of Rifaximin α Starting from Rifaximin β

5 Grams of rifaximin β having a 5.0% water content are dried under vacuum at +30° C. for 8 hours obtaining 4.85 g of rifaximin α having a 2.3% water content.

EXAMPLE 10

Preparation of Rifaximin β Starting from Rifaximin α

5 g of rifaximin α having a 2.5% water content are kept during 40 hours in an atmosphere containing a 56% relative humidity produced by means of a saturated aqueous solution of calcium nitrate tetrahydrate. 5.17 g of Rifaximin β with a 5.9% water content are obtained after this time.

What is claimed is:

1. A process for the production of rifaximin in polymorphic Form α, comprising:
   dissolving rifaximin in an alcoholic solvent at a temperature between approximately 45° C. and approximately 65° C.;
   precipitating the rifaximin by adding water to the alcoholic solvent to form a suspension and by lowering the temperature of the suspension to between approximately 0° C. and approximately 50° C.; and
   drying the rifaximin for a period of time between approximately 2 and approximately 72 hours to form rifaximin in polymorphic Form α,
   wherein the rifaximin Form α has a water content of between 3.0%-4.5%, and
   wherein the rifaximin Form α has x-ray powder diffraction pattern peaks at about 7.4°; 19.7°; 21.0° and 22.1° 2-θ.

2. A process for the production of rifaximin in polymorphic Form β, comprising:
   dissolving rifaximin in an alcoholic solvent at a temperature between approximately 45° C. and approximately 65° C.;
   precipitating the rifaximin by adding water to the alcoholic solvent to form a suspension and by lowering the temperature of the suspension to between approximately 0° C. and approximately 50° C.; and
   drying the rifaximin for a period of time between approximately 2 and approximately 72 hours to form rifaximin in polymorphic Form β,
   wherein the rifaximin Form β has a water content of between 4.5%-5.0%, and
   wherein the rifaximin Form β has x-ray powder diffraction pattern peaks at about 5.4°; 9.0°; and 20.9° 2-θ.

3. A process for the production of rifaximin in polymorphic Form γ, comprising:
   dissolving rifaximin in an alcoholic solvent at a temperature between approximately 45° C. and approximately 65° C.;
   precipitating the rifaximin by adding water to the alcoholic solvent to form a suspension and by lowering the temperature of the suspension to between approximately 0° C. and approximately 50° C.; and
   drying the rifaximin for a period of time between approximately 2 and approximately 72 hours to form rifaximin in polymorphic Form γ,
   wherein the rifaximin Form γ has a water content of from between 0% to 1%, and
   wherein the rifaximin Form γ has x-ray powder diffraction pattern peaks at about 5.0°, 7.1°, and 8.4° 2-θ.

4. The process of claim 1, further comprising washing the rifaximin Form α with water after precipitating.

5. The process of claim 1, wherein the alcoholic solvent is ethyl alcohol.

6. The process of claim 1, wherein said water added to precipitate the rifaximin is in a weight amount of between approximately 15% and approximately 70% with respect to the weight amount of alcoholic solvent used for the dissolution.

7. The process of claim 1, wherein after the addition of water, the temperature is lowered to between approximately 28° C. and approximately 32° C.

8. The process of claim 1, wherein the suspension is stirred at a temperature between approximately 40° C. and approximately 50° C. for a period of time between approximately 6 hours and approximately 24 hours.

9. The process of claim 1, where the temperature of the suspension is lowered to approximately 0° C. for a period of time between approximately 15 minutes and approximately one hour.

10. The process of claim 2, wherein the alcoholic solvent is ethyl alcohol.

11. The process of claim 2, wherein after the addition of water, the temperature is lowered to between approximately 28° C. and approximately 32° C.

12. The process of claim 2, wherein the suspension is stirred at a temperature between approximately 40° C. and approximately 50° C. for a period of time between approximately 6 hours and approximately 24 hours.

13. The process of claim 2, where the temperature of the suspension is lowered to approximately 0° C. for a period of time between approximately 15 minutes and approximately one hour.

14. The process of claim 3, further comprising washing the rifaximin Form γ with water after precipitating prior to drying.

15. The process of claim 3, wherein the alcoholic solvent is ethyl alcohol.

16. The process of claim 3, wherein said water added to precipitate the rifaximin is in a weight amount of between approximately 15% and approximately 70% with respect to the weight amount of alcoholic solvent used for the dissolution.

17. The process of claim 3, wherein after the addition of water, the temperature is lowered to between approximately 28° C. and approximately 32° C.

18. The process of claim 3, wherein the suspension is stirred at a temperature between approximately 40° C. and approximately 50° C. for a period of time between approximately 6 hours and approximately 24 hours.

19. The process of claim 3, where the temperature of the suspension is lowered to approximately 0° C. for a period of time between approximately 15 minutes and approximately one hour.

* * * * *

UNITED STATES PATENT AND TRADEMARK OFFICE
CERTIFICATE OF CORRECTION

PATENT NO. : 8,173,801 B2
APPLICATION NO. : 13/041346
DATED : May 8, 2012
INVENTOR(S) : Viscomi et al.

It is certified that error appears in the above-identified patent and that said Letters Patent is hereby corrected as shown below:

Title Page, Item (75) Inventor is corrected to read:
-- Giuseppe Claudio Viscomi, Bologna (IT);
Manuela Campana, Bologna (IT);
Dario Braga, Bologna (IT);
Donatella Confortini, Bologna (IT);
Vincenzo Cannata, Bologna (IT);
Paolo Righi, Bologna (IT);
Goffredo Rosini, Bologna (IT);
Denis Severini, Santarcangelo di Romagna (IT) --.

Signed and Sealed this
Eighteenth Day of August, 2015

Michelle K. Lee
*Director of the United States Patent and Trademark Office*